United States Patent
Binetti et al.

(10) Patent No.: US 8,119,791 B2
(45) Date of Patent: Feb. 21, 2012

(54) SI-RNA-MEDIATED GENE SILENCING TECHNOLOGY TO INHIBIT TYROSINASE AND REDUCE PIGMENTATION

(75) Inventors: Ralph R. Binetti, Stanford, CT (US); Brian C. Jones, Flower Mound, TX (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 12/361,576

(22) Filed: Jan. 29, 2009

(65) Prior Publication Data

US 2009/0202458 A1 Aug. 13, 2009

Related U.S. Application Data

(63) Continuation-in-part of application No. 10/738,413, filed on Dec. 17, 2003, now Pat. No. 7,504,385.

(51) Int. Cl.
C07H 21/04 (2006.01)
C07H 21/02 (2006.01)
A61K 48/00 (2006.01)

(52) U.S. Cl. .......... 536/24.5; 536/23.1; 514/44

(58) Field of Classification Search .......... None
See application file for complete search history.

(56) References Cited

U.S. PATENT DOCUMENTS

| | | | |
|---|---|---|---|
| 6,436,378 B1 * | 8/2002 | Mahashabde et al. | 424/59 |
| 6,573,050 B1 * | 6/2003 | Ben-David et al. | 435/6 |
| 2002/0141956 A1 * | 10/2002 | Perricone | 424/62 |
| 2004/0215006 A1 * | 10/2004 | Bennett et al. | 536/23.1 |

OTHER PUBLICATIONS

Caplen et al., dsRNA-mediated gene silencing in cultured Drosophila cells: a tissue culture model for the analysis of RNA interference, 2000, Gene, 252, pp. 95-105.*
Zhang et al., Targeted Gene Silencing by Small Interfering RNA-Based Knock-Down Technology, 2004, Current Pharmaceutical Biotechnology, 5, pp. 1-7.*
Elbashir et al. (The EMBO Journal, vol. 20, No. 23, 2001, pp. 6877-6888).*
Bertrand et al. (Biochemical and Biophysical Research Communications, 296, 2002, pp. 1000-1004).*

\* cited by examiner

*Primary Examiner* — Amy Bowman
(74) *Attorney, Agent, or Firm* — Joan M. McGillycuddy; Charles J. Zeller

(57) ABSTRACT

The present invention describes compositions and methods for treating, preventing and improving hyperpigmentation, or other unwanted pigmentation of the skin, or other unwanted skin condition, such as age spots, aged skin, skin discoloration, etc., wherein the compositions include siRNA-gene silencing oligomers specific for tyrosinase. The compositions are used to treat a broad variety of pigmentation conditions, and are preferably applied to the skin, or are delivered by directed means to a site in need thereof.

11 Claims, 1 Drawing Sheet

MEDIUM CONTROL
TRANSFECTION
MEDIA CONTROL
SiRNA for
TYROSINASE
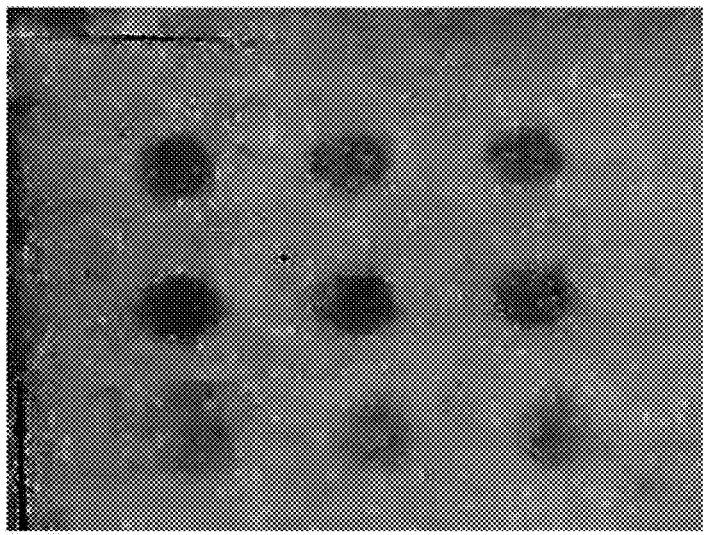

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 1

<400> SEQUENCE: 1
uaggaccugc cagugcucut t                                            21

```
<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 1

<400> SEQUENCE: 2
agagcacugg cagguccuat t                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 2

<400> SEQUENCE: 3
uaggaccugc cagugcucut t                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 2

<400> SEQUENCE: 4
agagcacugg cagguccuat t                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 3

<400> SEQUENCE: 5
uccuggaaac caugacaaat t                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 3

<400> SEQUENCE: 6
uuugucaugg uuuccaggat t                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 4

<400> SEQUENCE: 7
cacaccuguc uuugucuuat t                                             21

<210> SEQ ID NO 8
```

```
<211> LENGTH: 21
<212> TYPE: DNA
<213> ORGANISM: Artificial Sequence
<220> FEATURE:
<223> OTHER INFORMATION: Description of Combined DNA/RNA Molecule Pair:
      Synthetic Oligonucleotide Pair 4

<400> SEQUENCE: 8
ttguguggac agaaacagaa c                                              21
```

SI-RNA-MEDIATED GENE SILENCING TECHNOLOGY TO INHIBIT TYROSINASE AND REDUCE PIGMENTATION

CROSS-REFERENCE TO A RELATED APPLICATION

The present application is a continuation-in-part application of parent application U.S. Ser. No. 10/738,413, filed Dec. 17, 2003, which is incorporated herein by reference in its entirety.

FIELD OF THE INVENTION

The present invention relates to compositions and methods for skin and personal care involving the use of small interfering RNA (siRNA) oligomers for treating, preventing, or ameliorating hyperpigmentation, or other unwanted pigmentation, or other unwanted conditions in human skin. More particularly, the present invention relates to siRNA oligomers that inhibit the production of tyrosinase, a major enzyme involved in melanin production. The invention further relates to methods of delivery for such compositions so as to allow the siRNA oligomers to more readily reach the skin layer to improve the aesthetic appearance of the skin.

BACKGROUND OF THE INVENTION

Human skin color is determined primarily by the content of the pigment melanin in the basal epidermis layer. Melanin is synthesized by the process of melanogenesis within melanocytes (pigment-producing cells). Melanin is deposited onto melanosomes, which are transferred to keratinocytes in the basal epidermal layer. Melanosomes present in these basal keratinocytes are the key determinants of skin color. The keratinocytes leave the basal layer and undergo differentiation forming the cornified top layer of the skin. Once the keratinocytes leave the basal layer, the melanosomes lose their characteristic electron dense structure, and the load of melanin is carried to the surface of the skin by the differentiating keratinocytes.

The skin can become hyperpigmented when too much melanin concentrates at one area or portion of the skin due to the retention time of the melanosomes in the basal layer. Hyperpigmentation can also occur as a result of overexposure to the sun or other inflammatory stimuli. Hyperpigmentation can take the form of solar lentigines (age spots), ephilides (freckles), melasma, chloasma, and pigmented keratoses.

The prior art discloses ways to treat hyperpigmentation by application of skin lightening agents. Representative skin lightening agents include hydroquinone and Vitamin C. Such agents typically lighten the skin by inhibiting the expression of tyrosinase enzymes. Tyrosinase is a major enzyme involved in the synthesis of melanin in melanosome cells of humans and mice. Its activity is linked to, for example, hair and skin pigmentation, and hyperpigmentation, age spots, and uneven skin coloration.

A powerful tool used to study gene function in mammalian cells is the process of small interfering RNA (siRNA)-mediated gene silencing. siRNA gene silencing is directly related to the process of RNA interference (RNAi) that is currently being done in *Caenorhabditis elegans* species of nematode. The process uses double-stranded RNA that is less than 30 base pairs long, and has a sequence complementary to the messenger RNA (mRNA) targeted. As the siRNA crosses the plasma membrane, the reaction of the cell is to destroy the siRNA and any sequence exactly like it. Native mRNA will also be destroyed by the cell when the siRNA code is the same as a specific region found on the native mRNA. Thus, the siRNA "silences" expression of a gene product by specifically destroying its mRNA. Numerous groups describe methods of specifically targeting a variety of endogenously and exogenously expressed genes using siRNA. (Brummelkamp et al. (2002) Science, 296: 550-553; Elbashir et al. (2001) Nature, 411: 494-498; Paul et. al. (2002) Nature Biotech., 20:505-508; and Hannon, P. (2002) Nature, 418: 244-251). Gene silencing technology is also being applied in a broad range of therapeutic applications.

Safe, effective and new compositions containing siRNA oligomers to treat, prevent, reduce, inhibit, and/or improve hyperpigmentation, or other unwanted pigmentation in skin and hair, would be advantageous for the formulation of treatments and products for the skin. As described herein, novel and beneficial methods and compositions, as well as their mode of action, for the treatment of hyperpigmentation, or other unwanted pigmentation and the like, as well as for personal care products for the skin, are provided by the present invention.

SUMMARY OF THE INVENTION

In its broadest aspect, the present invention relates to compositions and methods comprising double-stranded small interfering RNA oligomers (siRNA) to inhibit the production of tyrosinase in a subject. The siRNA inhibit production of the tyrosinase protein by binding to a specific complement sequence found in the tyrosinase mRNA. As described above, tyrosinase is a major enzyme found in the pathway of melanin production; therefore, by inhibiting its formation, melanin and pigmentation decreases. Thus, the compositions and methods of the invention can be used to treat, including prevent, reduce, ameliorate and/or eliminate, hyperpigmentation and/or unwanted pigmentation in human skin, thereby improving the aesthetic appearance of skin.

In a specific embodiment, the present invention relates to an siRNA construct that is 21 oligonucleotides in length and has the following sequence:

```
5'-UAGGACCUGCCAGUGCUCUtt-3'

3'-ttAUCCUGGACGGUCACGAGA-5'.

5'-UAGGACCUGCCAGUGCUCUtt-3'

3'-ttAUCCUGGACGGUCACGAGA-5'

5'-UCCUGGAAACCAUGACAAAtt-3'

3'-ttAGGACCUUUGGUACUGUUU-5'

5'-CACACCUGUCUUUGUCUUAtt-3'

3'-ttGUGUGGACAGAAACAGAAC-5'
```

There are multiple sequences possible for the siRNA oligomers of the invention, but they preferably begin with two adenosines and are a total of 21 base pairs long. The first three siRNAs shown above are homologous to sequences found in both human and mouse forms of tyrosinase. The fourth siRNA is just one example of many from the human sequence of tyrosinase.

The siRNA for tyrosinase when applied to the skin will prevent, reduce, ameliorate and/or eliminate hyperpigmentation, or other unwanted pigmentation, or other unwanted conditions in human skin and hair, thereby lightening skin tone, bleaching or lightening hair, decreasing hyperpigmented states such as age spots, and improving skin discoloration.

It is to be understood that, as used herein, the terms treating and treatment include and encompass preventing, reducing, ameliorating, improving, alleviating, and/or eliminating hyperpigmentation, or other unwanted pigmentation of the skin, and the like. The present compositions and methods are also suitable for use in treating, as defined above, hyperpigmentation, or other unwanted pigmentation, of the skin and hair in numerous areas of the body, including, without limitation, the face, forehead, neck, arms, hands, legs, knees, feet, chest, back, groin, buttocks, and the like.

It is another aspect of the present invention to provide compositions, formulations and methods containing siRNA oligomers in the treatment of pigmentation, hyperpigmentation, unwanted hair pigmentation, age spots, and/or uneven skin tone, etc. These oligomers exert their effectiveness according to this invention by preferably crossing the plasma membrane of skin cells, wherein the siRNA and any sequence exactly like it (in this case, tryosinase mRNA) will be destroyed and degraded at the site of application, e.g., skin of the face, neck, arms, feet, or hands, particularly in the lower epidermis/upper dermis, and the layer of the skin where hair follicles/melanocytes interact. More specifically, the siRNA oligomers block or inhibit the native human tyrosinase mRNA, which, in turn, results in an inhibition of tyrosinase enzyme production and a reduction of pigmentation because the tyrosinase enzyme will not be present for melanin synthesis.

In addition, because it is understood that melanin synthesis is related to pigmentation, hyperpigmentation, hair pigmentation, age spots, etc., the inhibition, and/or the control or modulation of the proteins involved in melanin production by the newly-determined action of the siRNA oligomers as disclosed herein can serve a pivotal function in the treatment, prevention, reduction, amelioration, or elimination of unwanted pigmentation, and the like.

In accordance with this invention, the siRNA oligomers comprise compositions which include, without limitation, topically applied sunscreens, antioxidants, anti-inflammatories, cosmetics, including makeups, skin care actives, e.g, for fine lines and/or wrinkles and the like. Also in accordance with this invention, ingredients, components, or compounds that are formulated in such compositions in a variety of product forms, e.g., transdermals, such as patches, and the like, are encompassed, particularly for topical administration.

Another aspect of the present invention provides the compositions comprising the siRNA oligomers preferably for topical administration without inducing significant irritation. Further, such compositions are preferably delivered by, but not limited to, the use of targeted delivery systems, for example, liposomes, microspheres, transdermal patches, lipid or protein delivery systems, and the like, so that the actives can more readily reach and affect the melanin producing cells of the skin in the area of application, e.g., face, hands, or neck, or the dermal layer of the skin, where hair follicles are located. Compositions comprising siRNA oligomers, including liposome formulations, can be administered topically and through skin pores to deliver the siRNA oligomers to the sites requiring treatment.

In another of its aspects, the present invention provides compositions containing one or more siRNA oligomers and methods thereof which can improve the aesthetic appearance of the skin by treating, including preventing, eliminating, ameliorating and/or reducing at least one of the following: pigmentation, hyperpigmentation, age spots, dark circles under the eyes, hair pigmentation in an area where hair is not wanted, and mottled pigment. The improvement preferably results following topical application of a product or formulation containing an effective amount of one or more of the siRNA oligomers as described herein.

Another aspect of this invention provides a method of reducing, preventing, treating, or ameliorating one or more skin conditions due to dermatological aging or photoexposure of skin, comprising: topically applying a composition comprising one or more siRNA oligomers in an amount effective to reduce or block native tyrosinase mRNA, wherein the reduction or block of native tryosinase mRNA concomitantly reduces or blocks melanin production, thereby treating, preventing, reducing, ameliorating, or eliminating hyperpigmentation, or other unwanted pigmentation, or other unwanted skin condition.

Further aspects, features and advantages of the present invention will be better appreciated upon a reading of the detailed description of the invention.

BRIEF DESCRIPTION OF THE FIGURES

FIG. 1 presents the results of a Northern Blot experiment run to measure the amount of tyrosinase mRNA in B16 mouse melanoma cell line after 48 hours of treatment with a tyrosinase siRNA.

DESCRIPTION OF THE INVENTION

The present invention provides novel compositions and methods comprising siRNA oligomers herein found to be effective to treat, including prevent, reduce, ameliorate, inhibit, alleviate, and/or eliminate hyperpigmentation, or other unwanted pigmentation, due to dermatological aging of skin, due to chronological and/or hormonal aging, or due to photoexposure (e.g., to the sun, or ultraviolet radiation) of skin, and/or to improve the aesthetic appearance of skin.

More particularly, the present invention relates to the use of siRNA oligomers that are less than 30 oligonucleotides in length, more preferred between 15 and 30, more preferred between 19 and 25, and mostly preferred between 19 and 22 oligonucleotides in length, and have a sequence complementary to native human tyrosinase mRNA. In a specific embodiment, the present invention relates to an siRNA oligomer that is 21 oligonucleotides in length and has the following sequence:

```
5'-UAGGACCUGCCAGUGCUCUtt-3'

3'-ttAUCCUGGACGGUCACGAGA-5'.

5'-UAGGACCUGCCAGUGCUCUtt-3'

3'-ttAUCCUGGACGGUCACGAGA-5'

5'-UCCUGGAAACCAUGACAAAtt-3'

3'-ttAGGACCUUUGGUACUGUUU-5'

5'-CACACCUGUCUUUGUCUUAtt-3'

3'-ttGUGUGGACAGAAACAGAAC-5'
```

According to the present invention, yet without wishing to be bound by theory, the siRNA oligomers exert their effects by their ability to inhibit, block, reduce, or prevent the translation of native tyrosinase enzyme mRNA. The ability of the siRNA oligomers to inhibit or silence tyrosinase enzyme-production results in an inhibition or modulation of melanin production so as to decrease pigmentation in skin or hair, thereby, lightening hyperpigmentation, or other unwanted pigmentation, and the like.

Thus, in one of its embodiments, the present invention encompasses compositions, formulations and methods containing siRNA, herein determined to be useful in the treatment of hyperpigmentation, or other unwanted pigmentation of skin or hair. Skin or hair in a variety of areas of the body is amenable for treatment and/or receipt of the compositions of the present invention, including the face, forehead, neck, arms, legs, hands, feet, torso (chest), back, and the like.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly applied to the skin and enter cells, either by passive uptake or a delivery system of choice, such as described below. Some modes of synthesis include chemically synthesizing strands and annealing at a later date, in vitro transcription through the use of polymerase chain reaction (PCR) and Dnase digestion, or through the insertion of siRNA sequences in to plasmids (Brummelkamp et al. (2002) Science, 296:550-553; Jarvis et al., Ambion, Inc., poster published on the world wide web at ambion.com/techlib/posters/RNAi_0302.html)

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, and affinity purification with antibody can be used to purify siRNAs.

In a preferred embodiment, the siRNA oligomers are stabilized against degradation because of their double stranded nature and the introduction of Dnase/Rnase inhibitors. For example, the siRNA can be stabilized by including thymidine or uridine nucleotide 3' overhangs.

The siRNA contained in the compositions of the present invention can be chemically synthesized at industrial scale in large amounts. Methods available would be through chemical synthesis, or through the use of a biological agent.

The present invention encompasses compositions comprising one or more siRNA oligomers, preferably in a pharmaceutically-acceptable. cosmetic, or dermatological formulation which is suitable for contact with living animal tissue, including human tissue, and for topical administration, with virtually no adverse physiological effect, e.g., irritation, to the user. Thus, the inventive compositions are especially suitable for sensitive skin.

Compositions embraced by this invention can be provided in any cosmetically and/or dermatologically suitable form, for example, an emulsion, a cream, a mousse, a gel, a foam, a lotion, a mask, an ointment, a pomade, a solution, a serum, a spray, a stick, a patch, or a towelette. In addition, the compositions contemplated by this invention can include one or more compatible cosmetically acceptable additional ingredients, such as colorants, fragrances, emollients, humectants, preservatives, vitamins, thickeners, anesthetics, anti-acne agents, anti-allergenics, antifungals, antimicrobials, anti-inflammatory agents, anti-irritants, antineoplastics, antioxidants, antiseptics, antivirals, chelating agents, depigmenting agents, emulsifiers, exfollients, film formers, hypopigmenting agents, immune system boosting agents, immune system suppressing agents, insect repellents, lubricants, moisturizers, pharmaceutical agents, photostablizing agents, preservatives, retinoids, skin protectants, skin penetration enhancers, staining agents, sunscreens, stabilizers, surfactants, viscosity and/or rheology modifiers, and the like, as well as other botanicals such as aloe, chamomile, and the like, and as further described below. The compositions are applied topically for an effective period of time, preferably at least once or twice daily, for at least one week. The daily application can be for periods of up to two weeks, four weeks, or more.

The compositions of this invention can also be formulated into liposomes which can comprise other additives or substances, and/or which can be modified to more specifically reach or remain at a site following administration. Although the current system in use is a lipid based system, this invention also contemplates other delivery systems, for example, protein delivery systems or microspheres if the cell membrane is to be crossed.

Dermatologically acceptable compositions suitable for use in the present invention include compositions in which the active constituents, ingredients, or materials are contained in an amount effective to achieve the intended purpose. By way of example, in the present compositions, a siRNA oligomer is present in an amount of from about 0.0001 wt % to about 10 wt %, based on the total weight of the composition. More preferably, the present compositions include one or more siRNA oligomers in an amount from about 0.0005 wt % to about 5 wt %. Most preferably, the present compositions include one or more siRNA oligomers in an amount from about 0.001 wt % to about 1 wt % of the total composition.

The determination of an effective dose or amount is well within the capability of those skilled in the art. A therapeutically effective dose refers to that amount of siRNA oligomer identified in accordance with the present invention, which, for instance, treats, prevents, ameliorates, reduces, or eliminates hyperpigmentation, or other unwanted pigmentation, and the like. The practitioner, who will consider the factors related to the individual requiring treatment, will determine the exact dosage. Dosage and administration are adjusted to provide sufficient levels of the siRNA oligomer to bring about the desired effect. Factors which are typically considered include the severity of the degree of penetration into the skin, the individual's particular need, time and frequency of administration, drug combination(s), reaction sensitivities, and tolerance/response to treatment. Variations in dosage levels can be adjusted using standard empirical routines for optimization, as is well understood in the art. The range is usually between 1 nm to 100 µm (Elbashir et al. (2001) Nature, 411:494-498). Those skilled in the art will employ different formulations depending upon the nature, e.g., structure, composition, of the siRNA.

Embraced by the present invention are transdermal modes of delivery, such as patches and the like, with or without a suitable skin penetration enhancer. The methods and compositions embodied by the invention provide a means by which the siRNA oligomers can be effectively administered in a transdermal system. Frequently, compounds having poor topical absorption, or which are required at high dosage levels, are delivered transdermally. Accordingly, a transdermal means of delivering a composition or formulation (often with a skin penetration enhancer composition) to the skin is that of the transdermal patch or a similar device as known and described in the art. Examples of such devices are disclosed in U.S. Pat. Nos. 5,146,846, 5,223,262, 4,820,724, 4,379,454 and 4,956,171; such descriptions are not meant to be limiting.

The transdermal mode of storing and delivering the compositions onto the skin and forming the active composition is convenient and well suited for the purposes of an embodiment of the present invention. Preferably, when a topical patch is used, the patch is applied to the desired area for an extended period of time. Preferably, the extended period of time is greater than one hour; more preferably, the extended period of time is overnight, e.g., when the user is sleeping.

A particular embodiment of the present invention is directed to the delivery of the described compositions by the use of targeted delivery systems, for example, liposomes, microspheres (see, e.g., U.S. Pat. No. 5,770,222 to Unger et al.; Rozema, D. and Lewis, D. (2003) Targets, 2: 253-260), and the like, so that the siRNA can more readily reach and affect the skin cells of the area of application, e.g., face or neck, or the lower epidermis/upper dermis layer of the skin, where hair follicles and melanocytes are located together. Compositions comprising siRNA oligomers, including liposome formulations, can also be administered by direct injection subcutaneously or intradermally to more precisely deposit the active agents.

Liposomes and delivery systems and vehicles involving liposomes are well-known in the art. In brief, liposomes are unilamellar or multilamellar lipid vesicles which entrap a significant fraction of aqueous solution. The vesicular microreservoirs of liposomes can contain a variety of water-soluble materials, which are suspended within the emulsion (e.g., reviewed in G. Gregorius (Ed.), 1991, *Liposome Technology*, Vols. I, II, III, CRC Press, Boca Raton, Fla.; Davis S. S, and Walker I. M., 1987, *Methods in Enzymology*, 149:51-64; Mayhew E. et al., 1987, *Methods in Enzymology*, 149:64-77; and Shafer-Korting M. et al., 1989, *J. Am. Acad. Dermatol.*, 21:1271-1275). The preparation of liposomes and the variety of uses of liposomes in biological systems have been described (e.g., in U.S. Pat. No. 4,708,861 to M. C. Popescu et al., U.S. Pat. No. 4,224,179 to M. Schneider and U.S. Pat. No. 4,235,871 to D. P. Papahadjopoulos et al.). Accordingly, such liposomes can be formulated into any of the dermatological or cosmetic compositions as described herein.

The siRNA oligomers of the present invention can also be admixed, encapsulated, conjugated or otherwise associated with other molecules, molecule structures or mixtures of compounds, as for example, biodegradable polymers or receptor targeted molecules for topical and other formulations.

In addition to the siRNA as active agents, as described herein, the physiologically acceptable compositions can contain suitable physiologically acceptable carriers, diluents, or excipients comprising auxiliaries which facilitate processing of the siRNA oligomers into preparations which can be used cosmetically and/or pharmaceutically. Further details on techniques for formulation and administration are provided in the latest edition of *Remington's Pharmaceutical Sciences* (Mack Publishing Co.; Easton, Pa.). Compositions containing the siRNA oligomers of the present invention can be manufactured in a manner that is known in the art, e.g., by means of conventional mixing, dissolving, granulating, dragee-making, levigating, emulsifying, encapsulating, entrapping, or lyophilizing processes.

A preferred embodiment of the topical compositions of the present invention may also include at least one of the following: a surface smoother, a skin plumper, an optical diffuser, a sunscreen, an exfoliation promoter, or an antioxidant.

A surface smoother provides the functional benefits of enhancing skin smoothness and reducing the appearance of fine lines and coarse wrinkles. Examples include, without limitation, isopropyl myristate, petrolatum, isopropyl lanolate, silicones (e.g., methicone, dimethicone), or any mixtures thereof. The surface smoother is preferably present from about 0.1 wt % to about 50 wt % of the total weight of the composition. A skin plumper serves as a collagen enhancer to the skin. An example of a suitable and preferred skin plumper is palmitoyl oligopeptide. Other nonlimiting examples of skin plumpers include collagen and/or glycosaminoglycan (GAG) enhancing agents. The skin plumper is preferably present from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 wt % to about 20 wt % of the total weight of the composition.

In another embodiment, the present invention embraces a sunscreen that protects skin from damaging ultraviolet rays. Illustratively, the sunscreen provides both UVA and UVB protection by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixture or combination thereof. Preferably, the sunscreen is present from about 1 wt % to about 30 wt % of the total weight of the composition. In particular, the addition of a sunscreen is preferred to prevent/reduce the photodegradation of the composition and/or ingredients therein while in the package and/or on the skin after application.

It will be appreciated that the compositions of the present invention containing sunscreen bring about additional improvements to the aesthetic appearance of skin, including at least one of the following: minimizes sunburning, minimizes tanning, reduces redness, and reduces future wrinkle development. It will be appreciated that when the topical composition is intended to be applied prior to retiring for the evening, the addition of a sunscreen agent may not be required.

The present compositions may also have one or more skin active agents, such as exfoliation promoters. Suitable examples that can be used in the present compositions include keratolytic agents, i.e., an active agent having desquamating, exfoliant, or scrubbing properties, or an active agent which can soften the horny layer of the skin; alpha (α) and/or beta (β) hydroxy acids; benzoyl peroxide; keto acids, such as pyruvic acid, 2-oxopropanoic acid, 2-oxobutanoic acid, and 2-oxopentanoic acid; oxa acids, as disclosed in U.S. Pat. Nos. 5,847,003, 6,069,169, 5,932,229 and 5,834,513, the disclosures of which are incorporated herein by reference; urea; retinoids, or any mixtures thereof. These anti-wrinkle or anti-fine line active agents can be formulated, for example, in amounts of from about 0.0001% to 5% by weight relative to the total weight of the composition.

More specifically, examples of hydroxy acids include, but are not limited to, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methoxybenzoic acid. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof. Preferred skin active agents are 3,6,9-trioxaundecanedioic acid, glycolic acid, lactic acid, or any mixtures thereof.

When the present invention includes a skin active agent, the composition typically includes about 0.5 wt % to 30 wt %, preferably about 1 wt % to about 15 wt %, more preferably about 2 wt % to about 10 wt %, and most preferably about 4 wt %, of the skin active agent based on the total weight of the composition.

An antioxidant functions, among other things, to scavenge free radicals from skin to protect the skin from environmental agressors. Examples of antioxidants that can be used in the present compositions include compounds having phenolic hydroxy functions, such as ascorbic acid and its derivatives/ esters; beta-carotene; catechins; curcumin; ferulic acid derivatives (e.g., ethyl ferulate or sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Compositions of the present invention can include an antioxidant preferably from about 0.001 wt % to about 10 wt %, and more preferably from about 0.001 wt % to about 5 wt %, of the total weight of the composition.

The compositions of this invention can also include one or more ingredients, additives, or adjuvants as described in detail above. The amounts of these various ingredients are those that are conventionally used in the cosmetic or pharmaceutical fields, for example, they can constitute from about 0.01% to 20% of the total weight of the composition. In addition, these ingredients can be introduced into the fatty phase, into the liquid phase, and/or into lipid vesicles, depending on their nature.

The component(s) of the present invention are preferably contained in a cosmetically acceptable medium (i.e., vehicle, diluent or carrier). In an embodiment embracing topical application, the compositions of this invention comprise a medium that is compatible with human skin. The compositions can be formulated as aqueous, alcohol, or aqueous/ alcohol-based solutions, ointments, lotions, gels, water-in-oil, oil-in-water, or water-oil-water triple emulsions having the appearance of a cream or gel, microemulsion, or aerosol. In addition, the compositions can be in the form of vesicular dispersions containing ionic and/or nonionic lipids, as described above.

In one embodiment, the present invention relates to the administration of an effective amount of at least one siRNA oligomer or composition comprised thereof to inhibit, block, or silence tyrosinase enzyme production in skin and to reduce hyperpigmentation, or other unwanted pigmentation, or other skin condition.

In another embodiment, the present invention encompasses a method of treating hyperpigmentation, or other unwanted pigmentation, or other dermatological effects of aging or photoexposure of skin, comprising applying to skin a composition containing a siRNA specific for tyrosinase in a cosmetically and/or dermatologically acceptable medium, and in an amount effective to treat, reduce, prevent and/or ameliorate hyperpigmentation, or other unwanted pigmentation, or other skin condition. The application of the siRNA-containing composition is preferably topical. In addition, the composition is preferably applied via a directed mode of delivery, for example, by topical application of an aqueous composition or transdermal patch.

Another embodiment of the present invention relates to a method of improving the aesthetic appearance of skin and comprises applying to the skin, or introducing via a directed mode of delivery, a composition including one or more siRNA oligomer in an amount effective to improve the aesthetic appearance of the skin. According to this embodiment, the improvement in aesthetic appearance includes, but is not limited to, the treatment of at least one condition, such as pigmentation, hyperpigmentation such as age spots, unwanted hair pigmentation, dark circles under the eyes, and uneven skin coloration.

Example

The following example illustrates a specific aspect of the invention. The example should not be construed as limiting the invention, as the example merely provides specific understanding and practice of the invention and its various aspects.

FIG. 1 presents the results of a Northern Dot Blot experiment run to measure the amount of tyrosinase mRNA seen in B16 mouse melanoma cell line after a 48 hour treatment with a tyrosinase siRNA.

The contents of all patents, patent applications, published articles, abstracts, books, reference manuals and abstracts, as cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A cosmetic composition comprising:
one or more siRNA oligomers in an amount effective to ameliorate, reduce, and/or eliminate skin hyperpigmentation or other unwanted skin pigmentation; and a topical cosmetically acceptable vehicle, wherein the siRNA oligomer consists of:
5'-UAGGACCUGCCAGUGCUCUtt-3' (SEQ ID NO: 1) and
3'-ttAUCCUGGACGGUCACGAGA-5' (SEQ ID NO: 2).

2. The composition according to claim 1, wherein the composition is a topical composition.

3. The composition according to claim 2, wherein the composition is an at least once daily applied composition.

4. The composition according to claim 1, wherein the one or more siRNA oligomer is present in an amount from about 0.0001 wt % to about 10 wt % of the total weight of the composition.

5. The composition according to claim 1, wherein the one or more siRNA oligomer is present in an amount from about 0.0005 wt % to about 5 wt % of the total weight of the composition.

6. The composition according to claim 1, wherein the one or more siRNA oligomer is present in an amount from about 0.001 wt % to about 1 wt % of the total weight of the composition.

7. The composition according to claim 1, wherein the vehicle is a cosmetically or dermatologically acceptable vehicle.

8. The composition according to claim 1, wherein the composition further comprises a sunscreen.

9. The composition according to claim 8, wherein the sunscreen is selected from the group consisting of avobenzone, cinnamic acid derivatives, octyl salicylate, oxybenzone, titanium oxide, zinc oxide and combinations thereof.

10. The composition according to claim 1, wherein the composition further includes an ingredient selected from the group consisting of an alpha hydroxy acid, a beta hydroxy acid, a keto acid, an oxa acid and an oxa diacid.

11. The composition according to claim 1, wherein the composition is administered via a transdermal patch.

* * * * *